United States Patent
Brian et al.

(10) Patent No.: US 7,022,284 B2
(45) Date of Patent: Apr. 4, 2006

(54) EXTRACORPOREAL BLOOD HANDLING SYSTEM WITH INTEGRATED HEAT EXCHANGER

(75) Inventors: Ben F. Brian, Menlo Park, CA (US); John Thomas Buckley, San Jose, CA (US); Jean-Pierre Dueri, Sunnyvale, CA (US); Mehrdad Farhangnia, Sunnyvale, CA (US); Steven K. Stringer, Los Gatos, CA (US)

(73) Assignee: Cardiovention, Inc., Santa Clara, CA (US)

( * ) Notice: Subject to any disclaimer, the term of this patent is extended or adjusted under 35 U.S.C. 154(b) by 0 days.

(21) Appl. No.: 10/434,887

(22) Filed: May 9, 2003

(65) Prior Publication Data

US 2004/0223872 A1 Nov. 11, 2004

(51) Int. Cl.
*A61M 1/34* (2006.01)
*A61M 1/36* (2006.01)
*A61M 37/00* (2006.01)

(52) U.S. Cl. .......................... 422/46; 422/45; 604/6.11; 604/6.13; 604/6.14; 261/DIG. 28; 128/DIG. 3

(58) Field of Classification Search ............... 604/4.01, 604/6.09, 6.1, 6.11, 6.14; 422/44–48; 128/DIG. 3; 261/DIG. 28, 24, 28; 417/44.1, 420, 902; 96/10

See application file for complete search history.

(56) References Cited

U.S. PATENT DOCUMENTS

| 4,698,207 | A | 10/1987 | Bringham |
| 5,217,689 | A * | 6/1993 | Raible ......................... 422/46 |
| 5,266,265 | A | 11/1993 | Raible |
| 5,270,005 | A | 12/1993 | Raible |
| 5,770,149 | A | 6/1998 | Raible |
| 5,900,142 | A | 5/1999 | Maloney, Jr. et al. |
| 5,997,816 | A | 12/1999 | McIntosh et al. |
| 6,302,860 | B1 | 10/2001 | Gremel et al. |
| 6,337,049 | B1 | 1/2002 | Tamari |
| 6,428,747 | B1 | 8/2002 | Dueri et al. |
| 6,689,315 | B1 * | 2/2004 | Linker et al. ................. 422/45 |
| 6,730,267 | B1 | 5/2004 | Stringer et al. |
| 2004/0009097 | A1 * | 1/2004 | Stringer et al. ............... 422/45 |

* cited by examiner

*Primary Examiner*—Patricia Bianco
(74) *Attorney, Agent, or Firm*—Nicola A. Pisano, Esq.; Luce, Foward, Hamilton & Scripps LLP (57) ABSTRACT

Apparatus for oxygenating and pumping blood includes a housing defining a blood flow path including, in series, a gas collection plenum, a pump space and a blood oxygenation element. A pump disposed in the pump space is configured to draw blood from the gas collection plenum and propel blood from the pump space through a heat exchanger and the blood oxygenation element. The heat exchanger includes a heat exchange plate and a coolant space.

7 Claims, 13 Drawing Sheets

EXTRACORPOREAL BLOOD HANDLING SYSTEM WITH INTEGRATED HEAT EXCHANGER

FIELD OF THE INVENTION

The present invention relates to an extracorporeal blood handling system with an integrated heat exchanger.

BACKGROUND OF THE INVENTION

For more than thirty years, vascular diseases have been treated using open surgical procedures. In 1999 alone, 753,000 open-heart procedures, including coronary artery bypass grafting (CABG), valve replacements, and heart transplants, were performed. During a typical CABG procedure, a sternotomy is performed to gain access to the pericardial sac, the patient is put on cardiopulmonary bypass (CPB), and the heart is stopped using a cardioplegia solution.

Generally, previously-known CPB is accomplished by constructing an extracorporeal blood handling system including, inter alia, a venous line, a venous reservoir, a centrifugal or roller pump that perfuses blood through the extracorporeal circuit and the patient, an oxygenator for oxygenating the blood, an arterial line for returning oxygenated blood to the patient, and an arterial filter located in the arterial line.

Many extracorporeal blood handling systems also include a heat exchanger. Heat exchangers are generally used to cool the blood and lower the patient's body temperature during surgery. Reducing body temperature significantly lowers the demand for oxygen by the patient's vital organs. The blood is heated near the end of surgery to raise the body temperature.

Recently, the development of minimally invasive techniques for cardiac bypass grafting, for example, by Heartport, Inc., Redwood City, Calif., and CardioThoracic Systems, Inc., Cupertino, Calif., have placed a premium on reducing the size of equipment employed in the sterile field. Whereas open surgical techniques typically provide a relatively large surgical site that the surgeon views directly, minimally invasive techniques require the placement of endoscopes, video monitors, and various positioning systems for the instruments. These devices crowd the sterile field and can limit the surgeon's ability to maneuver.

At the same time, however, the need to reduce priming volume of the oxygenator and pump, and the desire to reduce blood contact with non-native surfaces has increased interest in locating the oxygenator and pump as near as possible to the patient.

In recognition of the foregoing issues, some previously known extracorporeal blood handling systems have attempted to miniaturize and integrate components including an oxygenator, heat exchanger and pump.

One problem with previously known extracorporeal blood handling systems is the difficulty in designing an extracorporeal blood handling system including an integrated heat exchanger having improved heat transfer efficiency.

Another problem with previously known extracorporeal blood handling systems is that the inclusion of an integrated heat exchanger necessitates additional priming volume.

A further problem with previously known extracorporeal blood handling systems is the difficulty in designing an extracorporeal blood handling system having an integrated heat exchanger that is integrated in such a way as to minimize the overall size of the extracorporeal blood handling system.

In view of the aforementioned limitations, it would be desirable to provide an extracorporeal blood handling system including an integrated heat exchanger having improved heat transfer efficiency.

It also would be desirable to provide an extracorporeal blood handling system including an integrated heat exchanger that does not require additional priming volume.

It would be also be desirable to provide an extracorporeal blood handling system including an integrated heat exchanger that is integrated in such a way as to minimize the overall size of the blood handling system.

It further would be desirable to provide an extracorporeal blood handling systems wherein the integrated heat exchanger provides dual functionality as a blood filter and a heat exchanger.

SUMMARY OF THE INVENTION

In view of the foregoing, it is an object of the present invention to provide an extracorporeal blood handling system including an integrated heat exchanger having improved heat transfer efficiency.

It is another object of the present invention to provide an extracorporeal blood handling system having an integrated heat exchanger that is integrated in such a way as to minimize the overall size of the extracorporeal blood handling system.

It is an additional object of the present invention to provide an extracorporeal blood handling system including an integrated heat exchanger that does not require additional priming volume.

It is a further object of the present invention to provide an extracorporeal blood handling system including an integrated heat exchanger that provides dual functionality as a blood filter and a heat exchanger.

These and other objects of the present invention are accomplished by providing an extracorporeal blood handling system having air removal, blood filtration, oxygenation, pumping and heat exchange capabilities in a low volume integrated housing. The apparatus comprises a housing defining a blood flow path including, in series, a gas collection plenum a pump space and a blood oxygenation element. A pump is disposed in the pump space, and is configured to draw blood from the gas collection plenum and to propel the blood from the pump space through the blood oxygenation element.

In a first family of embodiments, housing is configured so that a heat exchanger disposed in the blood flow path between the gas collection plenum and the pump space. In a second family of embodiments, the heat exchanger is disposed within the housing in a compartment on the outlet side of the pump space.

In a first embodiment, the heat exchanger comprises a heat exchange surface and a coolant space, wherein the heat exchange surface separates the coolant space from the pump space and provides a conductive medium through which coolant within coolant space can transfer heat to the blood in the pump space. Advantageously, since heat is transferred to blood within pump space, no additional priming volume is required to prime the apparatus. Preferably, the coolant space includes a plurality of coolant channels formed by baffles, wherein the coolant channels are configured to distribute coolant over the heat exchange plate and increase contact time between the coolant and heat exchange surface, thereby improving heat exchange efficiency.

In a second embodiment, the heat exchanger preferably comprises a multiplicity of hollow tubes or fibers disposed within the gas collection plenum. The tubes serve as both a heat exchanger and the first stage of a progressive blood filter that filters air and particulate matter from the blood. Blood is drawn by the pump through the lumens of the tubes, while coolant is passed circumferentially about the exterior of the tubes.

In an alternative family of embodiments, the apparatus comprises a housing defining a blood flow path including, in series, a gas collection plenum, a pump space, a heat exchanger and a blood oxygenation element. A pump disposed in the pump space draws blood from the gas collection plenum and propels it from the pump space through the heat exchanger and the blood oxygenation element. The heat exchanger preferably comprises a bellows including a corrugated wall having a blood-contacting surface and a coolant-contacting surface. The wall provides a conductive medium through which coolant adjacent to the coolant-contacting surface can transfer heat to blood adjacent to the blood contacting surface.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Overview of a Preferred Blood Handling System

Figure 1:
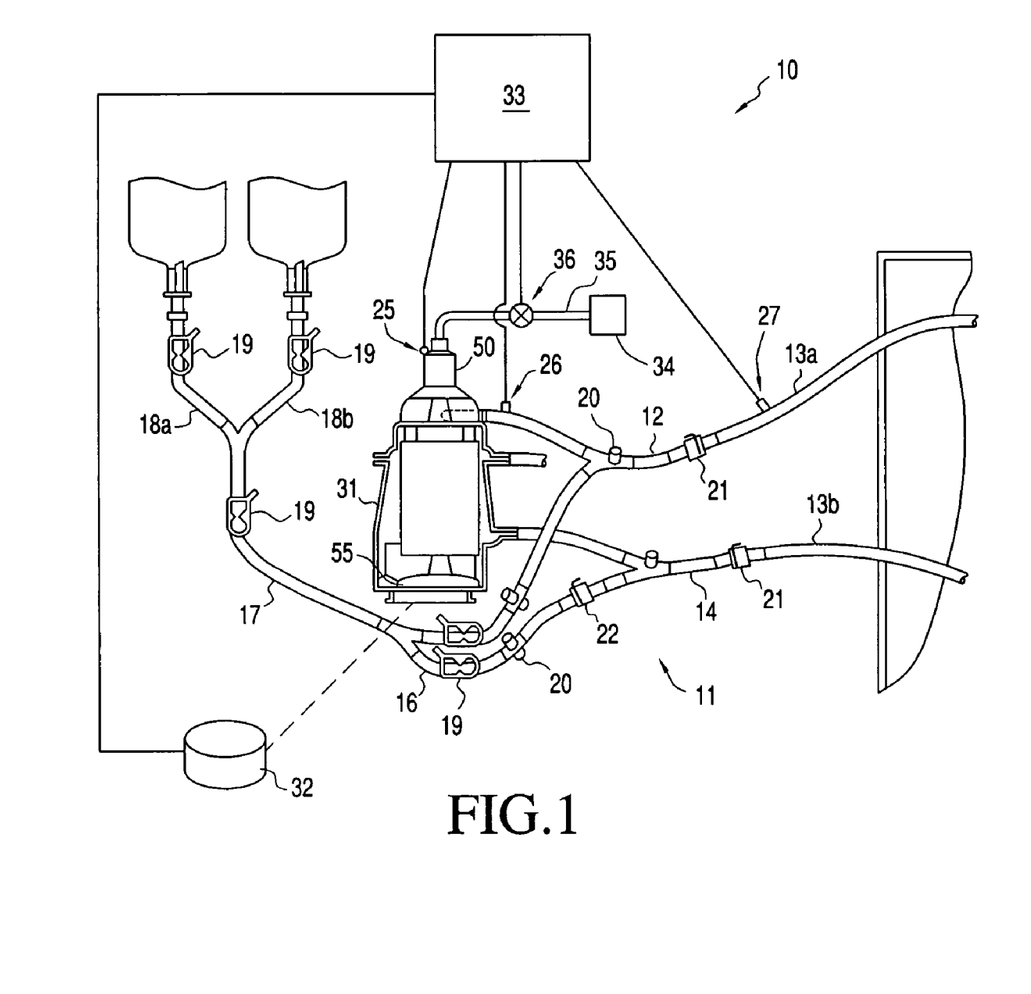
FIG. 1 is a schematic view of a preferred extracorporeal circuit suitable for use with the heat exchanger of the present invention.

Referring to FIG. 1, a preferred extracorporeal blood handling system 10 suitable for use with the heat exchanger of the present invention is described. Extracorporeal blood handling system 10 is designed to maintain a patient on full or partial bypass support, for example, during a coronary artery bypass graft procedure or mitral valve repair procedure, in either a full-bypass or beating heart mode of operation.

Extracorporeal blood handling system 10 includes an extracorporeal blood circuit 11 having a perfusion circuit comprising venous line 12, perfusion line segments 13a, 13b and arterial line 14, and a priming circuit comprising line 16, priming line 17, and segments 18a and 18b. The ends of perfusion line segments 13a, 13b are shown extending into the sterile field as they would appear during use, where they are coupled to venous and arterial cannulae respectively.

Extracorporeal blood circuit 11 illustratively includes pinch clamps 19 and sampling manifolds 20 disposed on various of the lines. Quick-disconnect couplings 21 are provided at the junctions of venous line 12 and venous segment of perfusion line 13a and arterial line 14 and arterial segment of perfusion line 13b. These couplings 21 permit venous line 12 to be directly coupled to arterial line 14 during priming. Quick-disconnect coupling 22, provided in line 16, permits the inclusion of additional optional elements when the priming circuit is used for recirculation.

Extracorporeal blood handling system 10 further includes an integrated blood processing component 31 coupled to a drive unit 32 and controller 33. In addition, the blood handling system 10 includes a gas removal system including sensors 25–27, and valve 36 coupled to suction source 34 via line 35. The sensors 25–27, valve 36 and drive unit 32 preferably are electrically coupled to controller 33 so that controller 33 regulates operation of valve 36 and drive unit 32 in response to output of the sensors 25–27. As explained in greater detail hereinafter, the gas removal system of the present invention removes air and other gases from extracorporeal blood circuit 11 and blood processing component 31 during priming and operation of the bypass system.

Figure 2A:
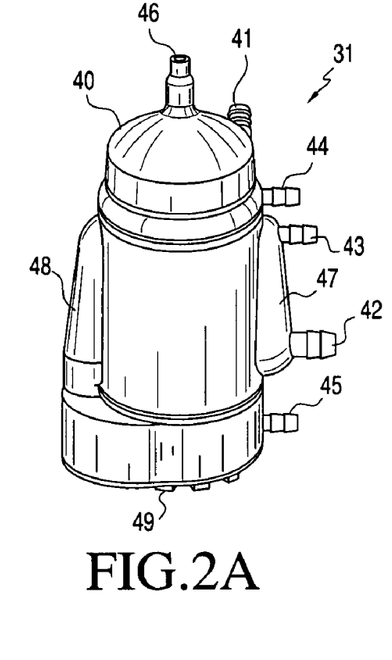
FIGS. 2A and 2B are, respectively, perspective and exploded views of a preferred blood processing component suitable for use with the heat exchanger of the present invention.
Figure 2B:
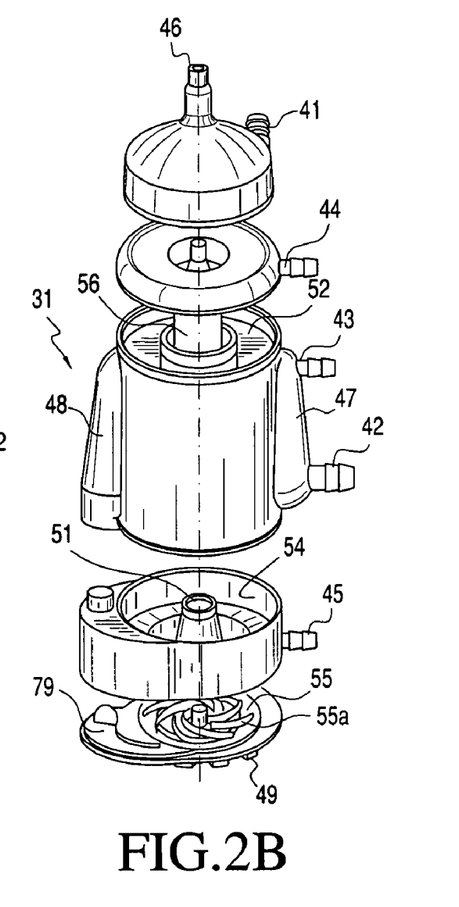
Figure 3:
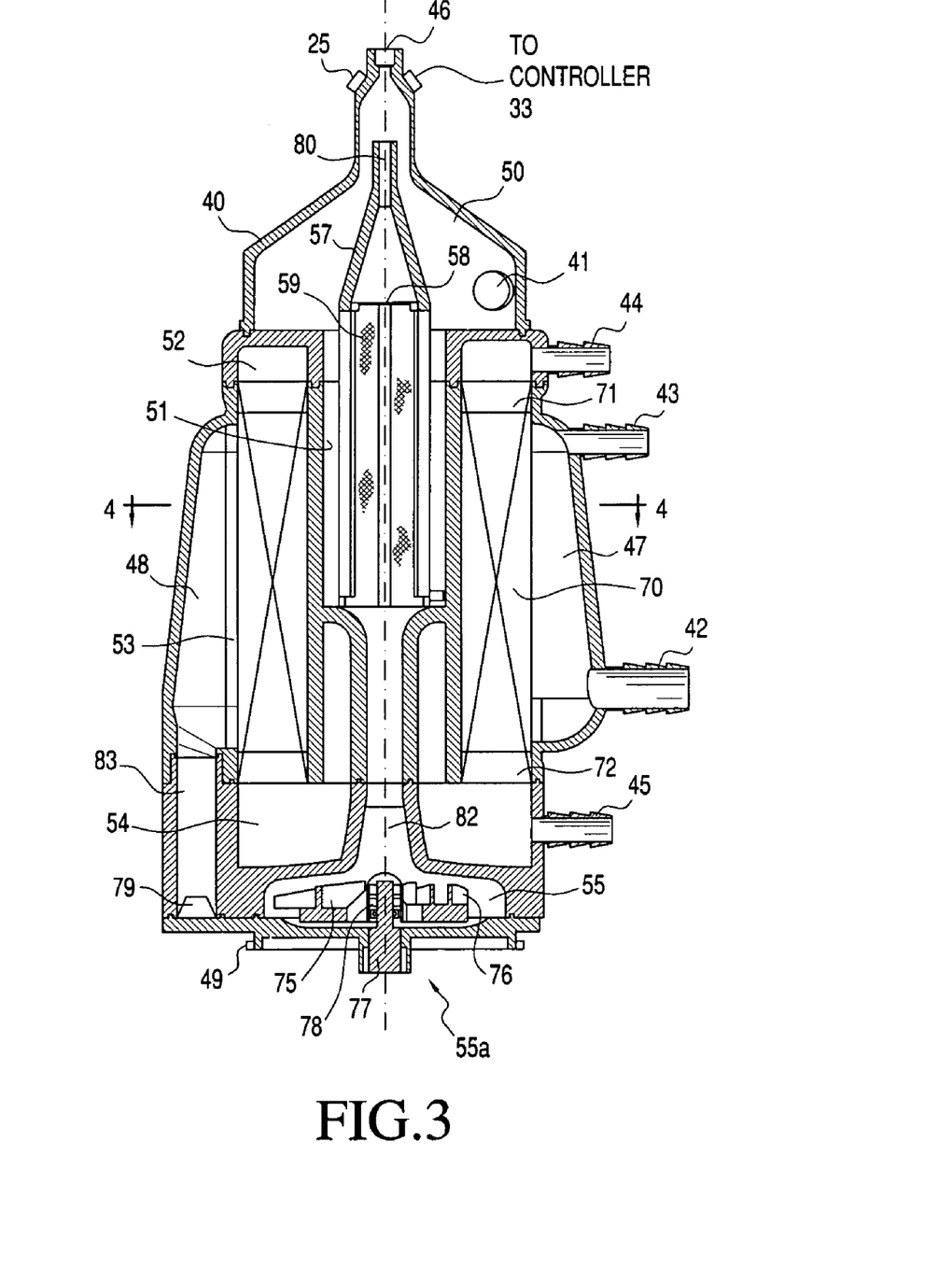
FIG. 3 is a side-sectional view of the blood processing component of FIGS. 2 and 3.

Referring now to FIGS. 2A, 2B and 3, integrated blood processing component 31 provides in a single disposable unit a blood oxygenator, blood pump, and blood filter, and optionally, a heat exchanger. Blood processing component 31 includes housing 40 having blood inlet 41, blood outlet 42, recirculation outlet 43, gas inlet port 44, gas outlet port 45 and gas removal port 46. Blood outlet 42 and recirculation outlet 43 are disposed from blood outlet manifold 47, which is located diametrically opposite blood inlet manifold 48 on housing 40. Blood processing component 31 preferably includes tabs 49 or other means for coupling blood processing component 31 to reusable drive unit 32.

Referring to FIG. 3, housing 40 comprises a series of compartments, including: gas collection plenum 50, central void 51, upper gas plenum 52, annular fiber bundle compartment 53, lower gas plenum 54 and pump space 55. In a preferred embodiment, central void 51 includes a larger diameter upper portion and a smaller diameter lower portion that couples to pump space 55.

Gas collection plenum 50 encloses a gas removal/blood filter 56 disposed within upper portion of central void 51. Filter 56 comprises generally conical, fluid impermeable upper wall 57 having outlet 80, baffled support structure 58 and filter material 59. Filter 56 causes gas entrained in blood introduced into the gas collection plenum to separate and collect in the upper portions of gas collection plenum 50. Blood inlet 41 is displaced tangentially relative to the centerline of housing 40, so that blood passing through blood inlet 41 into gas collection plenum 50 swirls around upper wall 57.

Upper wall 57 also preferably has a portion defining an interior chamber that communicates with the upper portion of gas collection plenum 50 through outlet 80. This configuration allows any gas that passes through filter material 59 to escape through outlet 80 in upper wall 57 and be evacuated from gas collection plenum 50. Advantageously, this feature facilitates rapid and easy priming of the blood processing component 31. In addition, low pressure caused by swirling of blood about upper wall 57 permits air-laden blood to recirculate through opening 80 into gas collection plenum 50.

Filter material 59 comprises one or multiple layers of a screen-like material, and is mounted to baffled support structure 58. Filter material 59 serves to exclude bubbles from the blood flow by maintaining the swirling action of the blood in the central void for a sufficient time to allow the bubbles to rise to the gas collection plenum. Because the blood circulates around the outside of gas removal/blood filter 56 in central void 51, bubbles impinge against filter material 59 tangentially, and thus "bounce off." Filter material 59 preferably also forms a first stage of a progressive blood filter that is distributed throughout the blood processing component, and may also serve to filter out relatively large particulate matter.

Figure 4A:
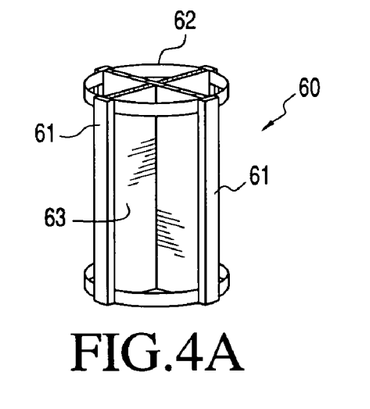
FIGS. 4A and 4B are, respectively, perspective and cross-sectional views of a filter element of the blood processing component of FIG. 3.
Figure 4B:
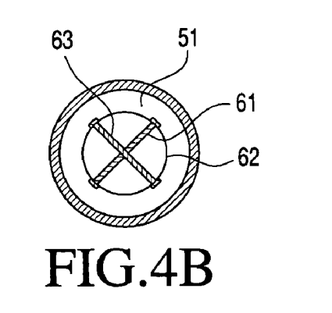

As illustrated in FIGS. 4A and 4B, support structure 58 forms a fluid impermeable cruciform structure 63 having longitudinal struts 61 and support rings 62. Struts 61 serve as baffles to reduce swirling of blood once the blood has passed through filter material 59.

Referring again to FIG. 3, blood oxygenation element 70 is disposed within annular fiber bundle compartment 53, and comprises a multiplicity of gas permeable fibers arranged in an annular bundle. As is well known in the art, the gas permeable fibers are potted near the upper and lower ends of the bundle so gas may pass through the interior of the fibers, while allowing blood to pass along the exterior of the fibers. The bundle of fibers has an upper potting region 71 that separates the blood flow region within the annular bundle from upper gas plenum 52, and lower potting region 72 that separates blood flow region from the lower gas plenum 54.

Blood passing into annular fiber bundle compartment 53 from blood inlet manifold 48 flows through blood oxygenation element 70 and to blood outlet manifold 47. The annular fiber bundle also provides some filtration of blood passing through blood processing component 31, by filtering out particulate matter that has passed through filter material 59 employed in gas removal/blood filter 56.

The lower portion of central void 51 communicates with pump space 55, in which pump 55a is disposed. In a preferred embodiment, pump 55a is a centrifugal pump including an impeller 75 having a plurality of vanes 76 and is mounted on shaft 77 via bearings 78. Impeller 75 preferably comprises an injection-molded part that encloses a ferromagnetic disk, so that the disk may be magnetically coupled to drive unit 32 (see FIG. 1). Blood flows through central void 51, through a pump inlet 82 and into pump space 55, where it is accelerated by impeller 75 and ejected via a pump outlet 83, which includes curved ramp 79. Ramp 79 serves to redirect radially outward blood flow from impeller to a longitudinal flow within blood inlet manifold 48.

In a preferred embodiment, oxygen is introduced into upper gas plenum 52 through gas inlet port 44 and passes through the interiors of the multiplicity of hollow fibers in blood oxygenation element 70. Carbon dioxide, any residual oxygen, and any other gases exchanged through blood oxygenation element 70 exits into lower gas plenum 54 and are exhausted through gas outlet port 45.

Referring again to FIG. 1, and in accordance with the present invention, the extracorporeal blood handling system 10 also includes sensors 25, 26 and 27 that monitor system parameters. Sensor 25 monitors the level of gas or blood in gas collection plenum 50. Sensor 26 detects the presence of gas in venous line 12; sensor 27 monitors the pressure in the venous line.

Sensor 25 is configured to sense a parameter indicative of a level or volume of air or other gas, or detect the absence of blood, and preferably operates by a non-contact method. Suitable sensor methods include electrical-charge based, optical and acoustic methods. A resistive contact method also could be employed, in which a low electrical current is passed between adjacent electrodes only in the presence of blood.

Sensor 25 preferably is a capacitance-type sensor that detects a change in electrical capacitance between the bulk of a liquid (in this case, blood or saline) and gas. Alternatively, sensor 25 may be optical in nature, and use a light source that has a wavelength that is minimally attenuated by blood. In this case, the light source is directed, at an oblique angle, through the blood towards a photodetector, and sensor 25 is positioned to detect the change in the refractive index of the blood (or saline prime) caused by the presence of air or other gases. In another alternative embodiment, sensor 25 may use an ultrasonic energy source and receiver to detect the presence of gas or absence of blood by the change in acoustic transmission characteristics.

The output of sensor 25 is supplied to controller 33 (see FIG. 1), which in turn regulates valve 36. When sensor 25 outputs a signal indicating that gas is present in the extracorporeal blood handling system 10, controller 33 opens valve 36, thereby coupling gas collection plenum 50 to suction source 34. Suction source 34 may be any suitable suction source such as a vacuum bottle, pump or standard operating room suction port. Once the gas is evacuated, and sensor 25 detects blood at an appropriate level, and changes its output so that controller 33 closes valve 36. In this manner, gas is continuously monitored and then automatically removed from the blood by the blood handling system 10.

Sensor 26 monitors for entrained air in the venous blood and comprises a sensor of the type described with respect to sensor 25. Preferably, sensor 26 uses ultrasound to detect the presence of air entrained in venous blood, and is coupled to controller 33 so that an output of the sensor is used to evaluate one or more trigger conditions, as described hereinafter. Sensor 26 also may be used as a back-up to sensor 25 in the event sensor 25 fails. Sensor 27 may be any suitable pressure sensor such as a piezoelectric transducer or an electrostatic capacitance sensor, and is also coupled to controller 33 and provides an output corresponding to the pressure in venous line 13a.

In operation, deoxygenated blood from the sterile field is routed through venous line 12 to blood inlet 41 of integrated blood processing component 31. Blood entering gas collection plenum 50 is induced to circulate around the exterior of filter 56 until air or other gases entrapped in the blood separate out of the blood and collect in the upper portion of the gas collection plenum 50. Responsive to the detection of the presence of a predetermined level or volume of gas by sensor 25, controller 33 controls operation of valve 36 to evacuate the gas.

The gas removal system incorporated in the system of FIGS. 1–3 is capable of removing large amounts of air from extracorporeal blood circuit 11 during initial startup, thereby reducing the time and manipulation required to prime the system. Advantageously, this feature facilitates rapid and easy set-up of blood handling system 10.

As blood circulates around filter 56 in central void 51, it is drawn by the negative pressure head created by impeller 75 through filter material 59 and down through central void 51 into pump space 55. Rotation of impeller 75 caused by drive unit 32, under the control of controller 33, propels blood up curved ramp 79 into blood inlet manifold 48.

From blood inlet manifold 48, the blood traverses blood oxygenation element 70 where it exchanges carbon dioxide and other gases for oxygen. Oxygenated blood then passes into blood outlet manifold 47. Oxygenated blood then is directed back to the sterile field through arterial line 14.

Figure 5:
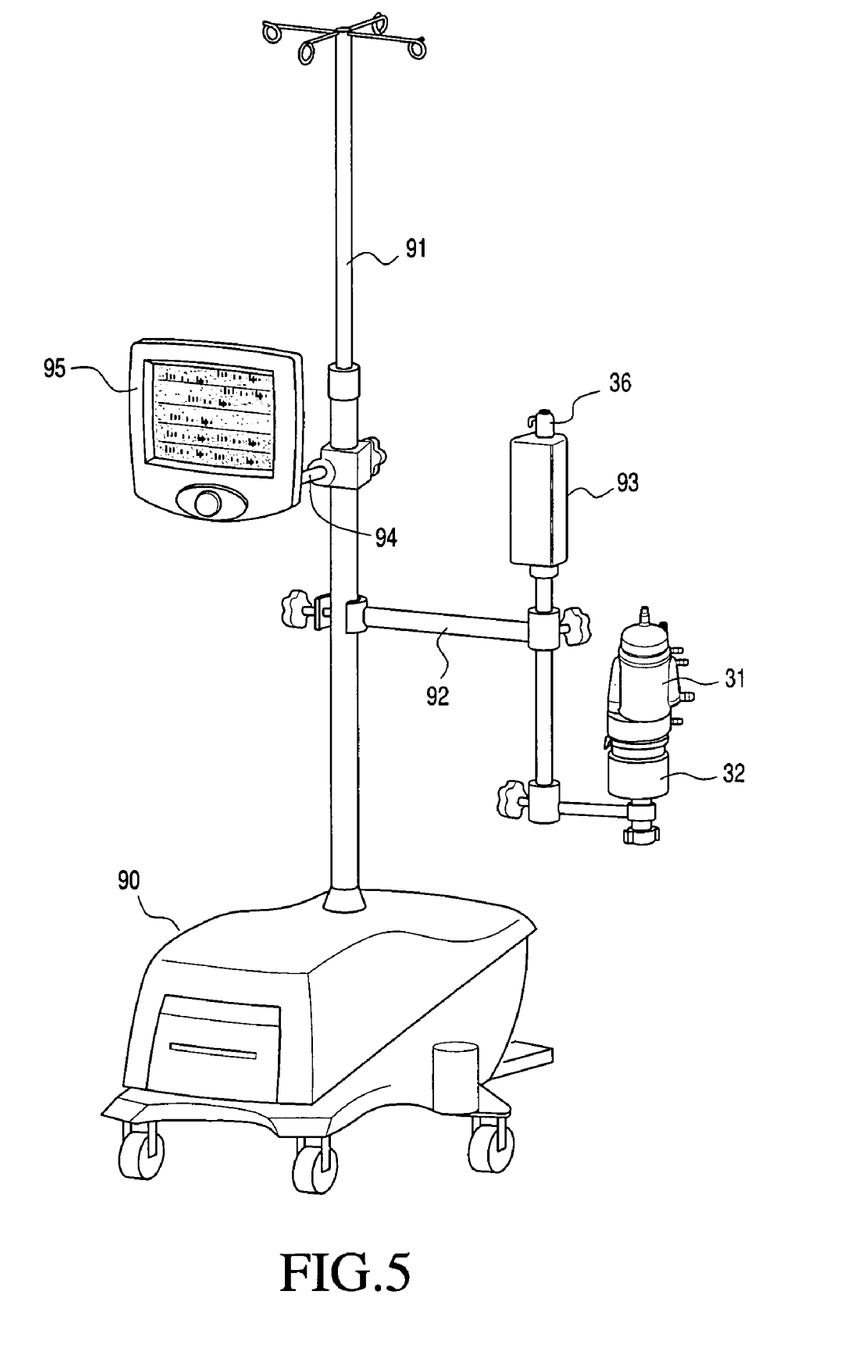
FIG. 5 is a perspective view of a preferred blood handling system suitable for use with the heat exchanger of the present invention.

FIG. 5 depicts a preferred embodiment of a blood handling system suitable for implementing the features of the present invention. All blood, gas and electrical lines have been omitted for clarity from FIG. 5, and microprocessor-driven controller 33 (see FIG. 1) and a back-up battery are enclosed in wheeled base 90. Pole 91 is mounted in base 90, and includes support arm 92 that supports blood processing component 31 on drive unit 32. Support arm 92 also carries solenoid 93 that controls valve 36, which is in turn coupled to suction source 34. Pole 91 also carries support arm 93, which carries display screen 95. Screen 95 preferably is a touch-sensitive screen coupled to the controller, and serves as both an input device for the extracorporeal blood handling system 10 and a display of system function.

Figure 6A:
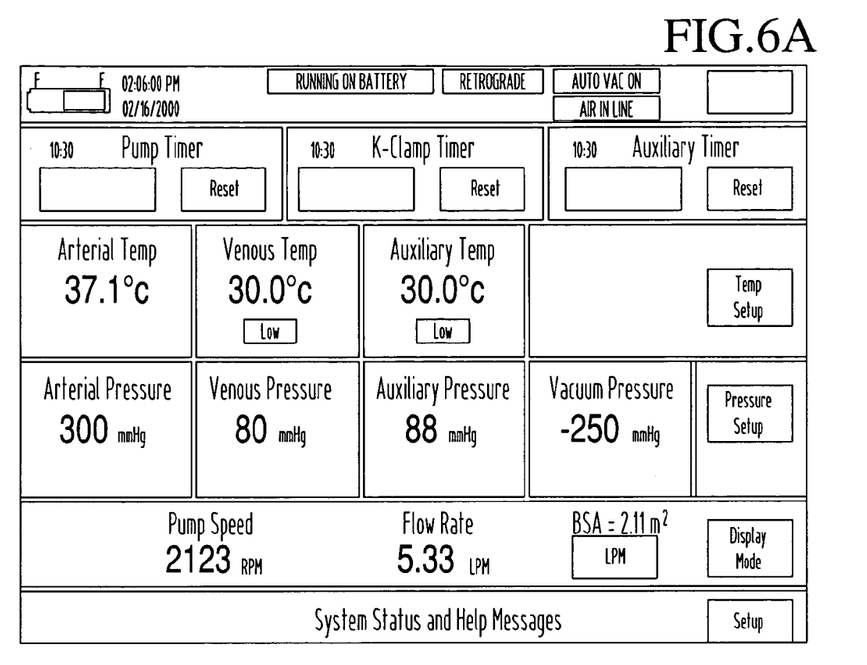
FIGS. 6A and 6B are, respectively, representative screens depicting the display of parameters monitored and/or controlled by the blood handling system of FIG. 5.
Figure 6B:
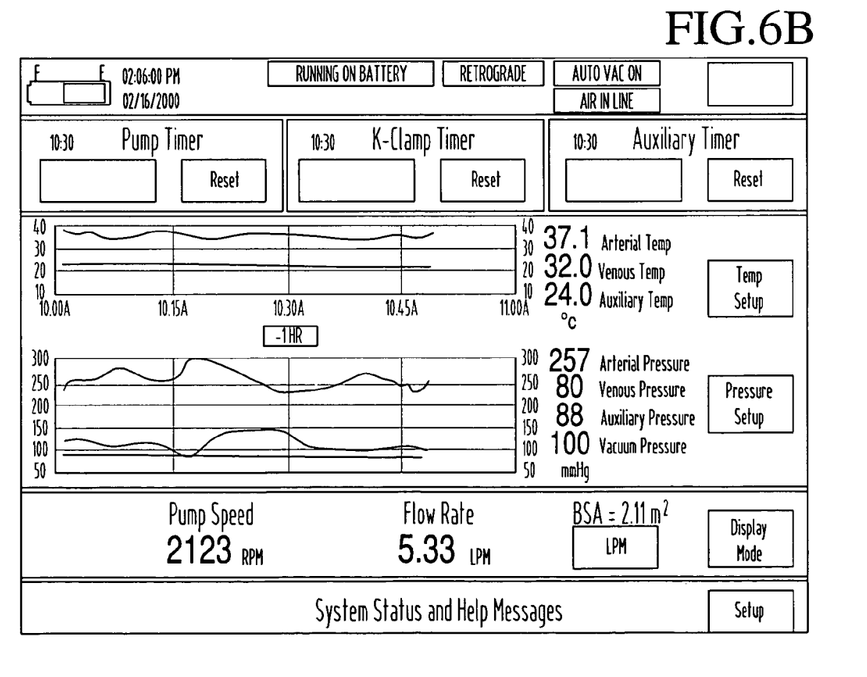
Figure 7:
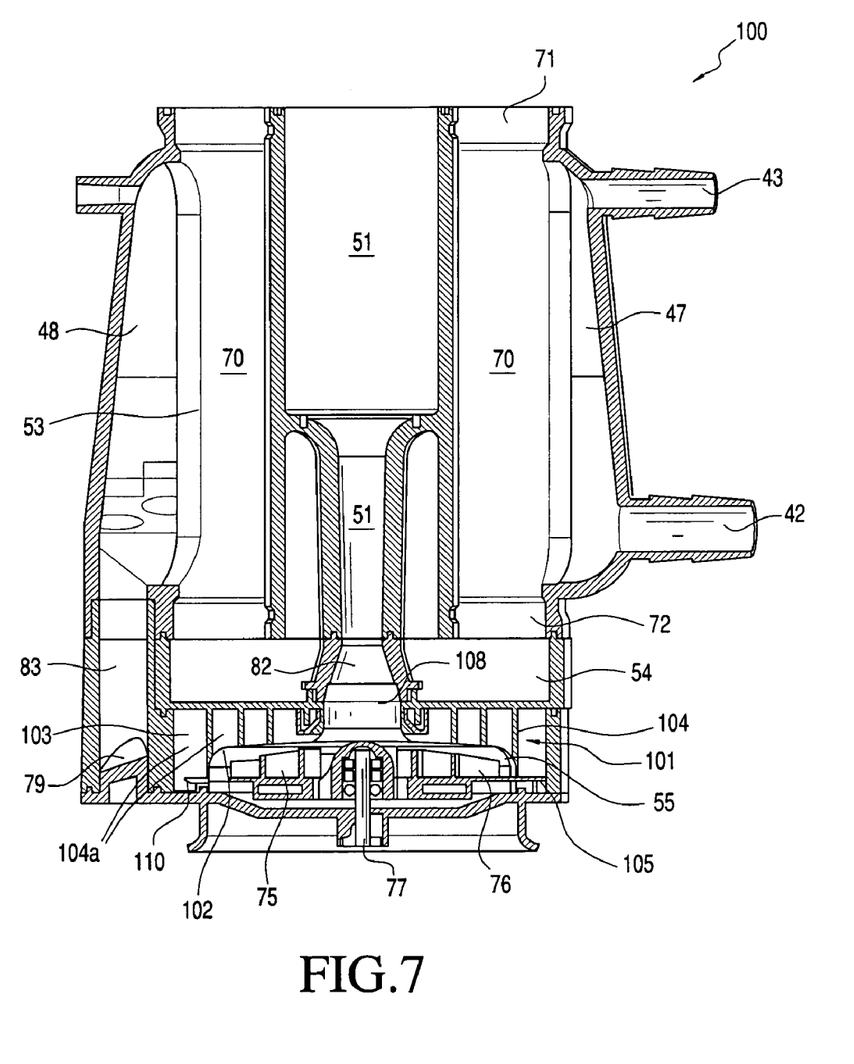
FIG. 7 is a side-sectional view of an embodiment of a first family of integrated blood processing components that include a heat exchanger disposed on the inlet-side of the pump.
Figure 8:
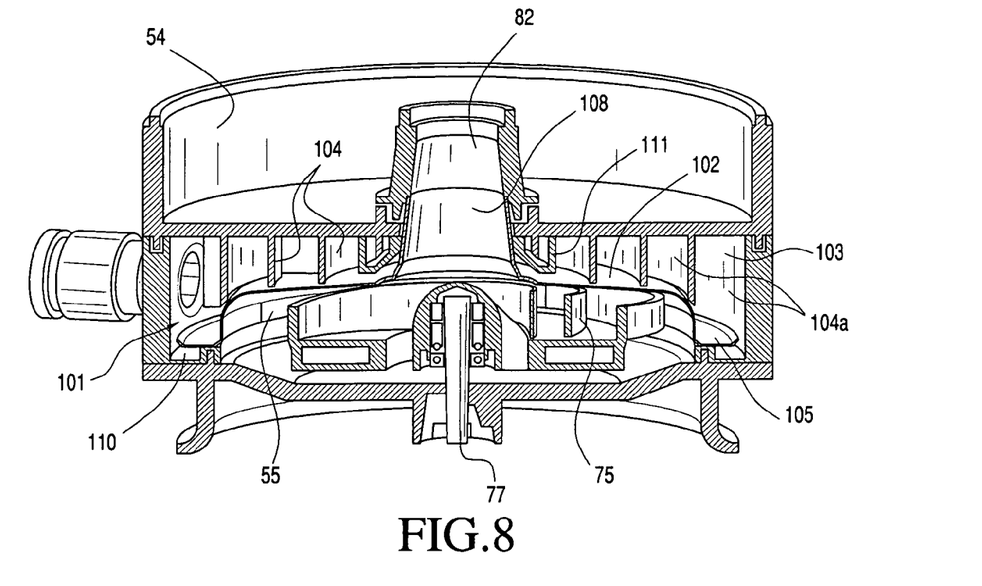
FIG. 8 is an enlarged side-sectional view showing the heat exchanger of FIG. 7.
Figure 9:
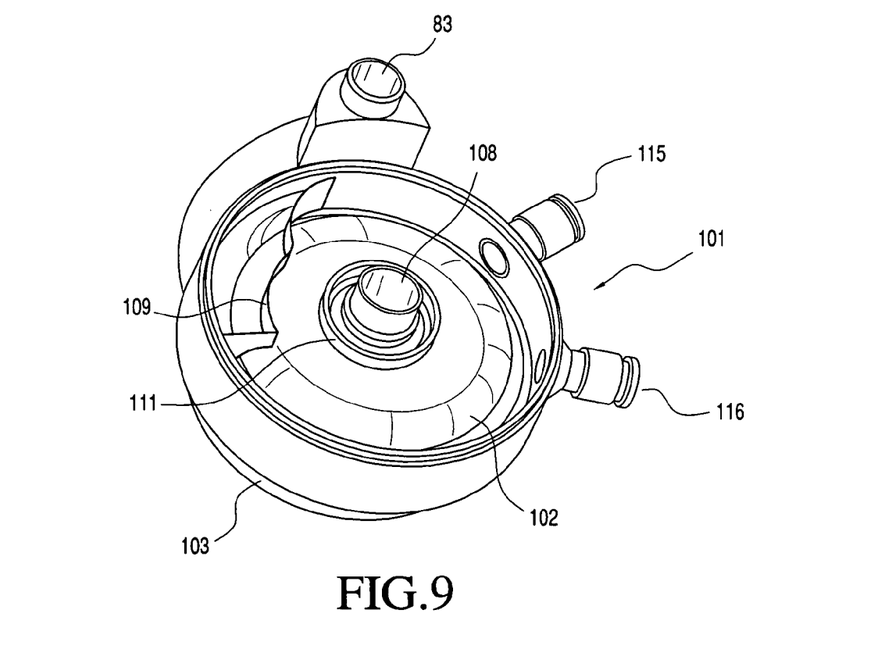
FIG. 9 is a top perspective view of the heat exchanger of FIG. 7.
Figure 10:
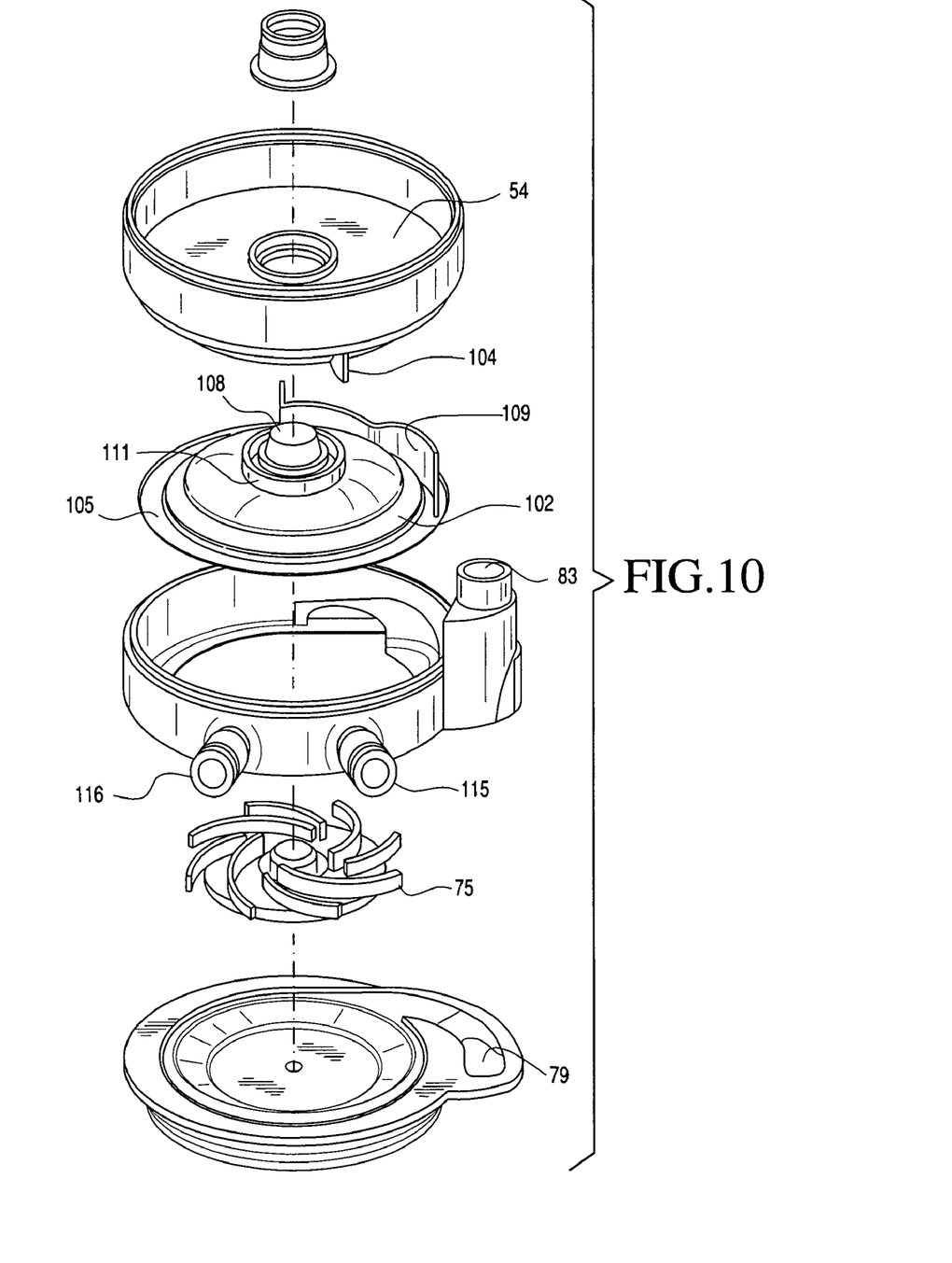
FIG. 10 is an exploded view of the heat exchanger of FIG. 7.
Figures 11, 12:
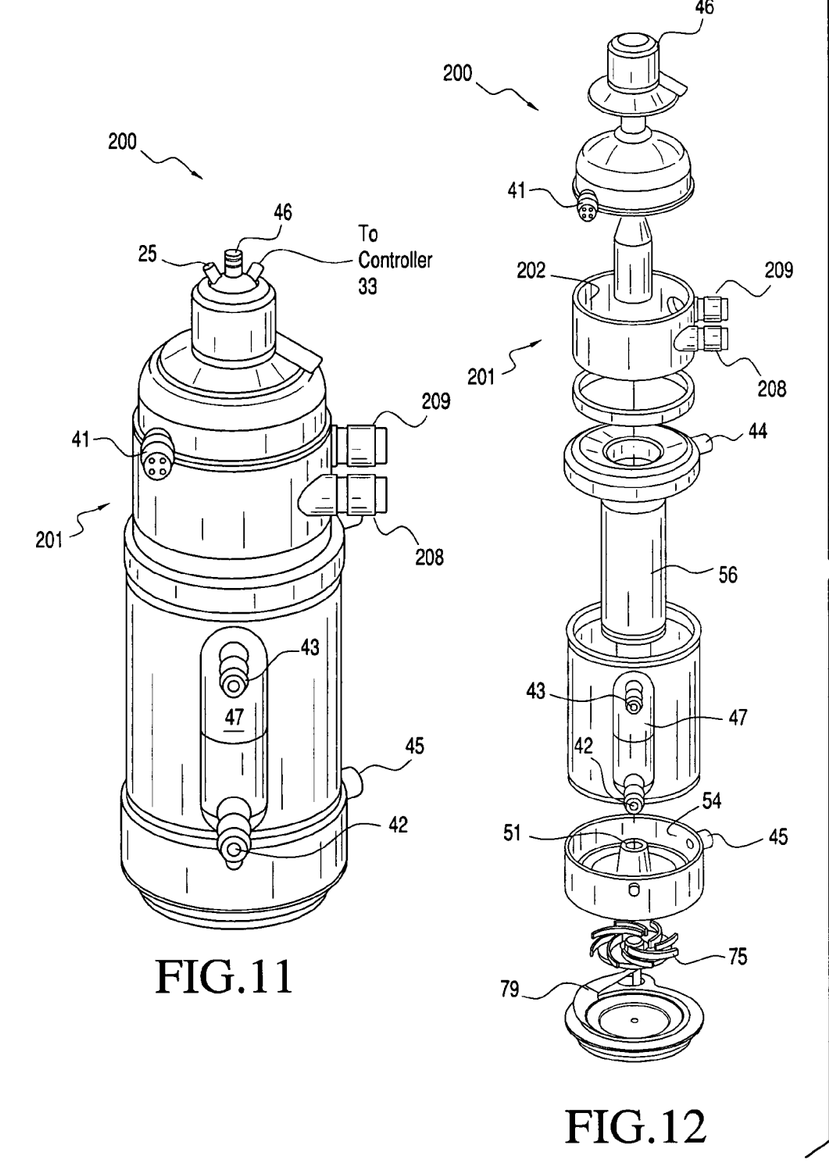
FIG. 11 is a perspective view of an alternative embodiment of the an integrated blood processing component of the present invention.
FIG. 12 is an exploded view of the blood processing component of FIG. 11.
Figure 13:
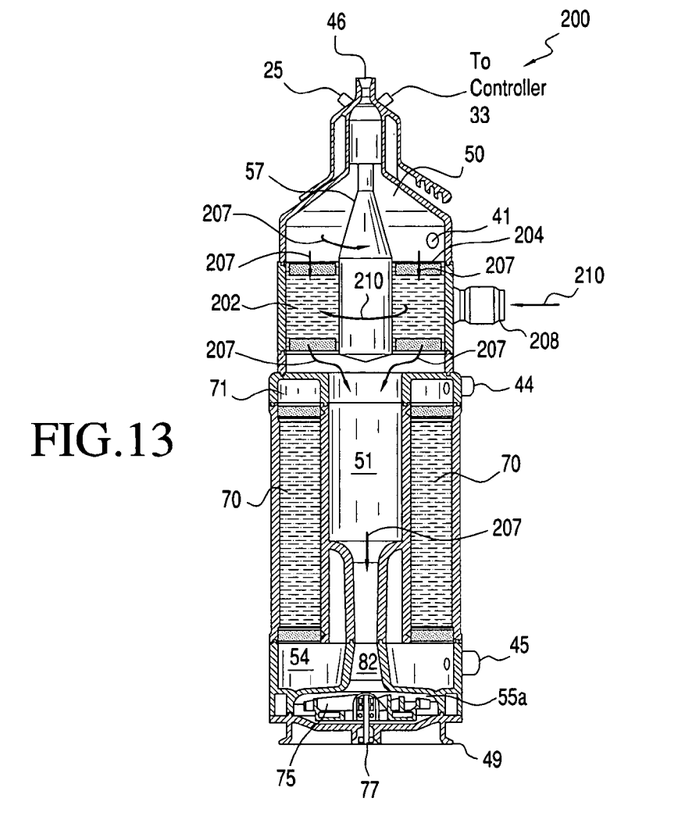
FIG. 13 is a side-sectional view of the blood processing component of FIG. 11.

FIGS. 6A and 6B provide representative samples of the information displayed on the main windows of the blood handling system 10. As will of course be understood by one of ordinary skill in the art of computer-controlled equipment, the software used to program operation of the controller may include a number of set-up screens to adjust particular system parameters. FIGS. 6A and 6B are therefore the windows that will most commonly be displayed by the clinician during a procedure.

The display of FIG. 6A includes an indicator of battery status, a series of timers for pump operation, duration of cross-clamping, and an auxiliary timer, arterial and venous temperatures and pressures, the speed of centrifugal pump 55a and the corresponding blood flow rate. Preferably, controller 33 is programmed with a number of algorithms for determining an appropriate blood flow rate during the procedure, as determined based on body surface area (BSA). The window also may display the value of BSA determined by the selected algorithm based on the patient's dimensions, and the suggested blood flow rate.

The display of FIG. 6B includes much of the same information provided in the window of FIG. 6A, but further shows temperatures and pressures graphically as well as numerically, so that the clinician can quickly identify trends in the data and take appropriate corrective measures. In addition, a lower portion of the windows displayed in FIGS. 6A and 6B may present system status or help messages, and include touch sensitive buttons that permit to access the other available functions.

Description of the Integrated Heat Exchanger of the Present Invention

In accordance with the principles of the present invention, an extracorporeal blood handling system includes an integrated heat exchanger for heating and/or cooling a patient's blood during a medical procedure. Two families of blood handling systems, each with illustrative embodiments, are described.

FIGS. 7–10 show a first embodiment of an extracorporeal blood handling system with integrated heat exchanger constructed in accordance with the principles of the present invention. In FIGS. 7–10, like components of the system of FIG. 3 have been numbered accordingly. In addition to the components described above with respect to blood handling component 31, blood processing component 100 also incorporates heat exchanger 101.

Heat exchanger 101 comprises heat exchange surface 102 that separates pump space 55 from coolant space 103. Preferably, heat exchanger 101 further comprises baffles 104 disposed within coolant space 103. Baffles 104 form a maze having coolant channels 104a that define a tortuous path for the flow of coolant, such as water. Advantageously, coolant channels 104a help distribute coolant evenly over the heat exchange surface and increase the contact time between the coolant and heat exchange surface 102, thus enhancing heat exchange. Heat exchange surface 102 thereby provides a conductive medium through which coolant flowing through baffles 104 may heat or cool the blood flowing within pump space 55.

Preferably, heat exchange surface 102 is a metal or metal alloy having high thermal conductivity and corrosion resistance, such as stainless steel. To enhance heat transfer, heat exchange surface 102 may have protrusions, e.g., dimples, fins, ridges, or the like, that increase the surface area available for heat exchange. The protrusions may extend into pump space 55, coolant space 103, or both. To further increase heat transfer, the heat exchanger preferably is arranged for counter-current flow, such that the blood and coolant flow in opposite directions on opposite sides of heat exchange surface 102.

Heat exchange surface 102 also includes cylinder 108 that defines pump inlet 82 and barrier 109 that encapsulates potting used to affix the heat exchange surface to blood processing component 100. Barrier 109 prevents potting from overflowing onto heat exchange surface 102, thereby ensuring that heat transfer efficiency is substantially maintained. Barrier 109 may be laser welded or brazed to heat exchange surface 102 along its contour. In addition, collar 111 is affixed by laser welding or brazing onto cylinder 108 to facilitate attachment of heat exchange surface 102 to blood processing component 100. Collar 111 also supports the floor of lower gas plenum 54. Baffles 104 optionally may be integrally molded with the floor of lower gas plenum 54.

In operation, coolant enters coolant space 103 via coolant inlet 115 and flows through channels 104a defined by baffles 104. After transferring heat to or absorbing heat from the blood, the coolant exits coolant space 103 via coolant outlet 116. Blood flows through gas removal/blood filter 56 and into pump space 55 via pump inlet 82. As impeller 75 draws blood through pump space 55, heat is transferred between the coolant and blood via heat exchange surface 102.

Convection between the blood and the heat exchange surface is enhanced by the action of impeller 75, which propels the flow of blood across the heat exchange surface. Thereafter, blood is propelled out of pump space 55 via pump outlet 83 to blood inlet manifold 48 and blood oxygenation element 70. Advantageously, since the blood is heated or cooled by heat exchanger 101 as the blood is driven through pump space 55, heat exchanger 101 does not increase the priming volume of the extracorporeal blood handling system.

Referring now to FIGS. 11–15 an alternative embodiment of the extracorporeal blood handling system with integrated heat exchanger is described. In FIGS. 15–19, like components of the embodiment of FIG. 3 have been numbered accordingly. In addition to the components described above with respect to blood handling component 31, blood processing component 200 also incorporates an integrated heat exchanger 201.

Heat exchanger 201 includes filter 202 (see FIGS. 14 and 15), preferably disposed entirely within gas collection plenum 50. Compared to the system of FIG. 3, central void 51 may be narrowed as the need for baffled support structure 58 is obviated, thereby maintaining approximately the same the total priming volume of the blood processing component 200. In accordance with the principles of the present invention, filter 202 serves substantially the same function as gas removal/blood filter 56, which may be omitted from central void 51 (see FIG. 13).

Figure 14:
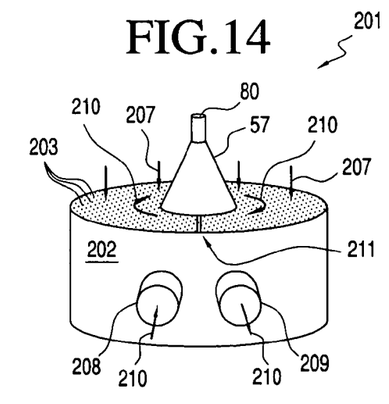
FIG. 14 is a perspective view of a heat exchanger suitable for use with the blood processing component of FIG. 11.
Figure 15:
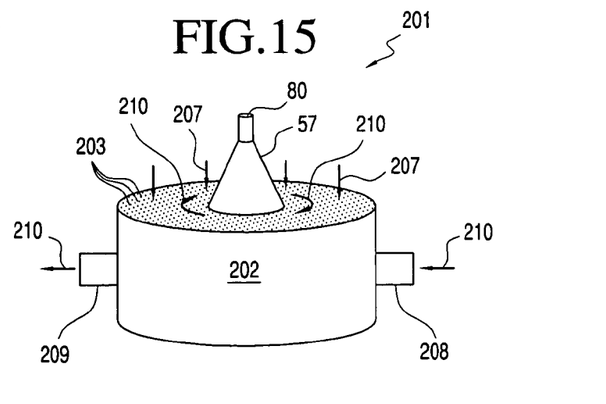
FIG. 15 is a perspective view of an alternative heat exchanger suitable for use with the blood processing component of FIG. 11.

Filter 202 comprises a multiplicity of vertically oriented hollow tubes or fibers 203. In a preferred embodiment, tubes 203 are non-porous membranes. Alternatively, tubes 203 may be formed of a suitable metal or metal alloy Blood is drawn through the lumens of fibers 203 by the negative pressure head created by impeller 75. As is well known in the art, the tubes are potted near the upper and lower ends of the filter so that blood may pass through the interior of the tubes, while allowing coolant to pass along the exterior of the tubes.

Preferably, filter 202 forms the first stage of a progressive blood filter. The blood oxygenation element disposed within annular fiber bundle compartment 53 also provides some filtration of blood passing through blood processing component 200, by filtering out air and particulate matter that has passed through filter 202. In addition, filter 202 optionally may include screen 204 to filter out larger particulate matter including impurities and air bubbles.

In operation, blood from blood inlet 41 enters gas collection plenum 50 tangentially and rotates about the top of the bundle of tubes 203 until it slows sufficiently for the blood to pass through the lumens of hollow tubes 203, through central void 51, and to pump 55a. As in the previous embodiment, rotation of blood entering gas collection plenum 50 causes air bubbles to "bounce off" the tops of the potted tube bundle and collect for subsequent evacuation. The blood flow through the system is indicated by arrows 207 in FIGS. 13–15. Coolant enters heat exchanger 201 via coolant inlet 208 and exits via coolant outlet 209. The path of coolant, as indicated by arrows 210, is circumferential the outside of tubes 203. The tubes provide a conductive medium through which the coolant may heat or cool the blood flowing within the tubes. Thus, heat exchanger 201 has dual functionality as both a mechanism for heat exchange and an air/blood filter.

Referring to FIG. 14, coolant inlet 208 and coolant outlet 209 are optionally located adjacent to each other on the side of filter 202. Filter 201 optionally may include an internal partition 211 so that coolant entering the heat exchanger must flow circumferentially around the perimeter of upper wall 57 before exiting via coolant outlet 209. Alternatively, as depicted in FIG. 15, coolant inlet 208 and outlet 209 may be located on opposite sides of the filter 202, so that partition 211 is not required to induce coolant to flow around the perimeter of upper wall 57.

Referring now to FIGS. 16–19 an illustrative member of a second family of embodiments of an extracorporeal blood handling system with integrated heat exchanger is described. In FIGS. 16–19, like components of the embodiment of FIG. 3 have been numbered accordingly. In addition to the components described above with respect to blood handling component 31, blood processing component 300 also incorporates heat exchanger 301, which comprises a metal bellows heat exchanger. Alternatively, heat exchanger 301 comprise a multiplicity of hollow tubes or fibers as described with respect to FIGS. 13 and 14, wherein the blood flows over the exterior of the tubes and the coolant passes through the lumens of the tubes.

Heat exchanger 301 comprises a bellows 301 having corrugated wall 302 defining an outer, blood-contacting surface 303 having a plurality of blood flow channels and an inner, coolant-contacting surface 304 defining a plurality of coolant flow channels. Corrugated wall 302 permits the transfer of heat from or to the blood adjacent to blood-contacting surface 203 to a coolant, such as water, flowing adjacent to coolant-contacting surface 304, depending upon the differential between blood and coolant temperatures.

Figure 16:
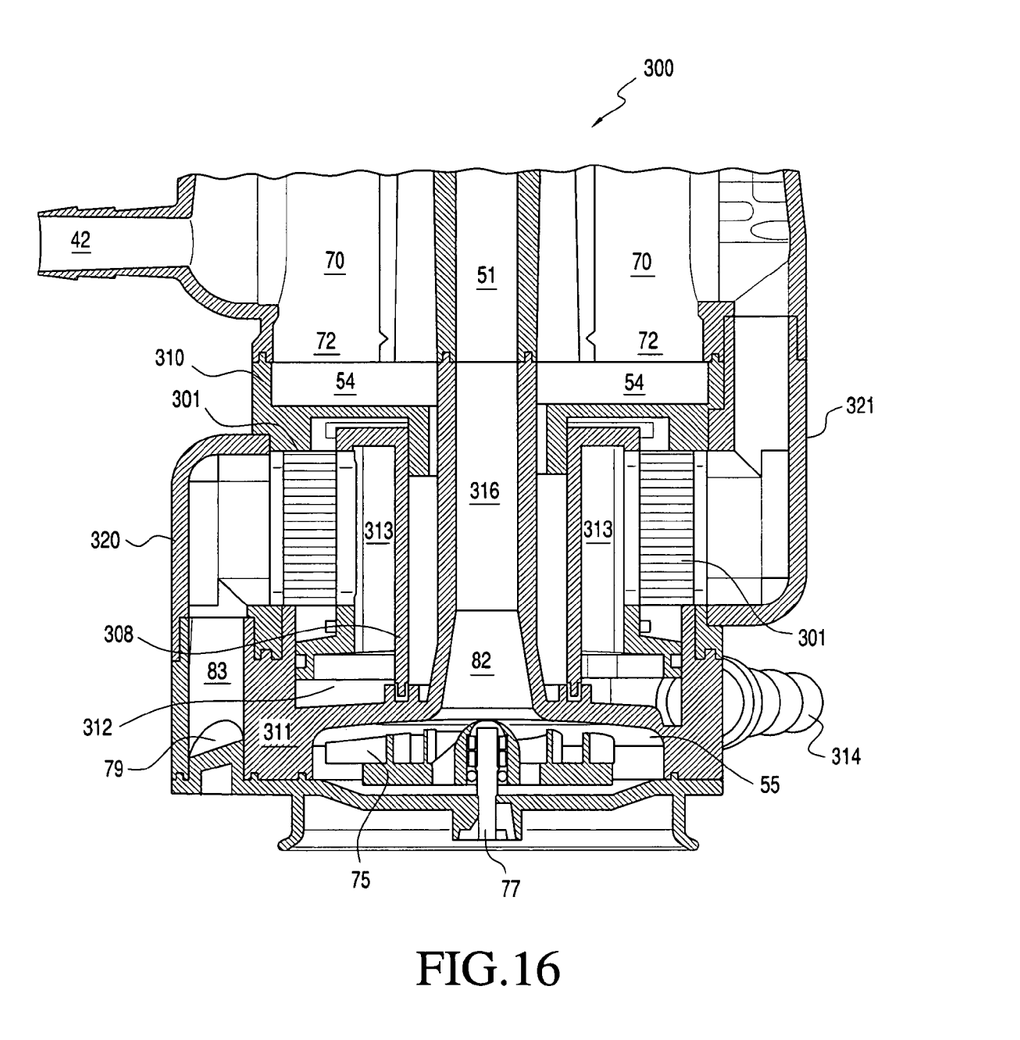
FIG. 16 is a side-sectional view of a second preferred embodiment of an integrated blood processing component including a heat exchanger according to the present invention.
Figure 18:
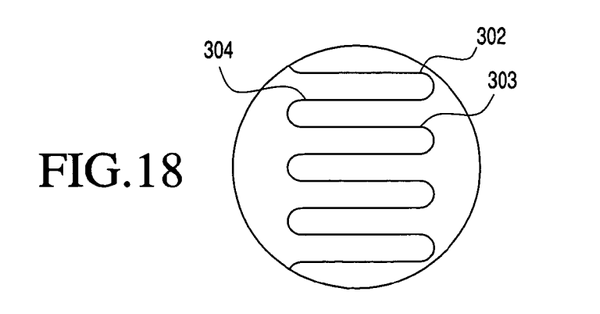
FIG. 18 is a magnified view of the wall of the heat exchanger of FIG. 16.

To improve heat transfer efficiency, heat exchanger 301 preferably is configured for counter-current flow, so that the blood and coolant flow in opposite directions on opposite sides of corrugated wall 302. As will be appreciated by those familiar with heat exchanger designs, forming channels in wall 302 also improves heat transfer efficiency by increasing the overall area available for heat transfer. In addition, as depicted in FIG. 18, the surfaces of the corrugations of wall 302 may be dimpled to further increase the area available for heat transfer.

Figure 17:
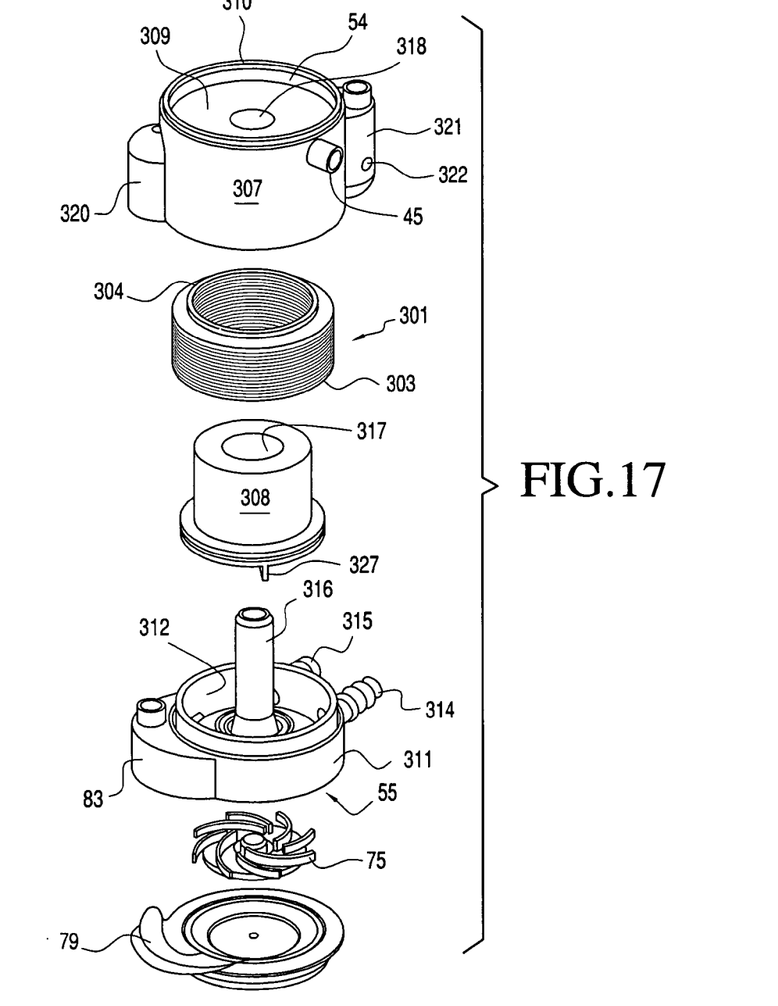
FIG. 17 is an exploded view of the heat exchanger of FIG. 16.

As best seen in FIG. 17, wall 302 is preferably a cylindrical wall formed from a thin sheet of highly thermally conductive, corrosion resistant material, e.g. stainless steel, that has been formed into a plurality of substantially parallel channels. The channels are accessible on alternating sides of wall such that blood flows through the channels interdigitated with channels through which coolant flows. Over a large surface area, the blood and coolant are only separated by the thickness of the wall, thereby enabling efficient thermal energy transfer.

Figure 19:
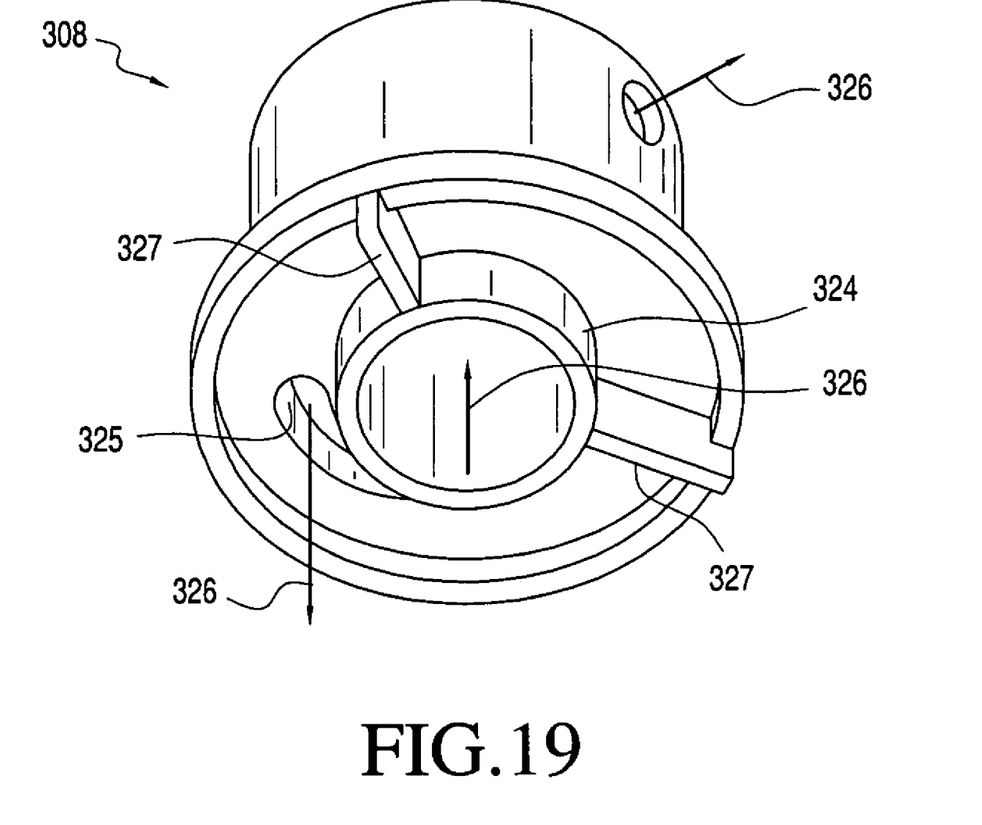
FIG. 19 is a perspective view of the heat exchanger core of the heat exchanger of FIG. 16.

Heat exchanger 301 is disposed between heat exchanger housing 307 and heat exchanger core 308. An upper portion of housing 307 forms top wall 309 and collar 310, which also defines lower gas plenum 54. Collar 310 includes gas outlet port 45 for purging residual gases from blood oxygenation element 70. Preferably, the outer diameter of the heat exchanger core has substantially the same shape (i.e., cylindrical) as heat exchanger 301 so that a coolant channel 313 is formed between core 308 and heat exchanger 301. By confining the flow of coolant to channel 313, the heat exchanger core forces the coolant to contact surface 304, thus improving heat transfer efficiency.

As shown in FIGS. 16 and 17, housing 307 is attached at its lower end to base portion 311. Base portion 311 separates coolant space 312 from pump space 55 and includes coolant inlet 314 and coolant outlet 315 in fluid communication with coolant space 312. Conduit 316 extends through central opening 317 in heat exchanger core 308 and aperture 318 on top wall 309 of housing 307 so that blood flows from central void 51, through heat exchanger 301 via conduit 316, and into pump space 55 via pump inlet 82.

Within pump space, impeller 75 accelerates and ejects the blood through pump outlet 83 and blood inlet manifold 320 into heat exchanger 301. Blood flows circumferentially around heat exchanger 301 in contact with blood-contacting surface 303. Depending upon the temperature of the fluid introduced into coolant space 312, heat exchanger 301 may be used to either transfer heat to or absorb heat from the blood. From the heat exchanger 301, blood flows up through blood outlet manifold 321 and into blood inlet manifold 48.

Preferably, blood outlet manifold 321 includes well 322 housing a temperature probe, so that the temperature of blood exiting the blood handling system may be monitored and the results displayed by the controller on the display screen. This feature advantageously may be employed with any of the above-described embodiments.

Referring now to FIG. 19, heat exchanger core 308 includes inlet conduit 324 for coolant flow to the coolant-contacting surface of heat exchanger 301 and outlet conduit 325 for coolant flow back into coolant space 312. Coolant flow within the heat exchanger core is indicated by arrows 326. The heat exchanger core preferably includes a pair of partitions 327 for separating coolant entering through inlet 314 from coolant exiting coolant space 212 via outlet 315.

In operation, coolant enters coolant space 312 via coolant inlet 314, and is guided by partitions 327 inlet conduit 325. After transferring heat to or absorbing heat from the blood, the coolant flows through outlet conduit 325 into coolant space 312. Partitions 327 then guide the coolant to coolant outlet 315.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for oxygenating and pumping blood comprising:
   a housing defining a blood flow path including, in series, a gas collection plenum, a pump space and a blood oxygenation space;
   a blood oxygenation element disposed in the blood oxygenation space;
   a solenoid-controlled valve coupled to the gas collection plenum to selectively evacuate gas from the gas collection plenum;
   a pump disposed in the pump space, the pump configured to draw blood from the gas collection plenum and propel blood from the pump space through the blood oxygenation element; and
   a heat exchanger comprising a metal alloy disposed and cooperating with the housing to define a wall surface of the pump space.

2. The apparatus of claim 1, wherein the wall surface separates a coolant space from the pump space.

3. The apparatus of claim 2, wherein the heat exchanger adds no additional priming volume to the apparatus.

4. The apparatus of claim 1, wherein the wall surface includes protrusions that increase a surface area available for heat exchange.

5. The apparatus of claim 2, wherein the coolant space includes a plurality of baffles that distribute coolant over the wall surface in the coolant space.

6. The apparatus of claim 1, wherein the pump draws blood from the gas collection plenum across the surface.

7. The apparatus of claim 1, wherein the heat exchanger is configured for counter-current flow in which blood and coolant flow in opposite directions on opposing sides of the wall surface.

* * * * *